United States Patent [19]

Workman

[11] 4,447,423
[45] May 8, 1984

[54] PEDICULICIDE COMPOSITION AND METHOD OF USE

[76] Inventor: Lester J. Workman, P.O. Box 5547, Sarasota, Fla. 34277

[21] Appl. No.: 459,035

[22] Filed: Jan. 18, 1983

Related U.S. Application Data

[63] Continuation-in-part of Ser. No. 249,696, Mar. 31, 1981, Pat. No. 4,374,853.

[51] Int. Cl.$^3$ .............................................. A61K 31/61
[52] U.S. Cl. .................................................... 424/234
[58] Field of Search ................. 424/230, 233, 234, 235

[56] References Cited

U.S. PATENT DOCUMENTS 2,664,382  12/1953  Omohundro et al. ............... 424/192

OTHER PUBLICATIONS

Eddy–J. of Invest Dermatol. vol. 12 (1949) pp. 117–123.
Merck Manual–12th edit. (1972), pp. 1455–1457, 1632–1635.
Goodman & Gilman–Pharmacological Basis of Therapeutics–5th edit. (1975), pp. 1012–1015.

Primary Examiner—Sam Rosen
Attorney, Agent, or Firm—Cushman, Darby & Cushman

[57] ABSTRACT

Body lice are effectively yet safely controlled with a pediculicide composition composed of dioctyl sodium and/or calcium sulfosuccinate and benzyl salicylate in an alcohol medium, the components desirably present in an approximate ratio of 1:1:2, respectively.

6 Claims, No Drawings

PEDICULICIDE COMPOSITION AND METHOD OF USE

CROSS REFERENCE TO RELATED APPLICATION

This application is a continuation-in-part of my earlier application Ser. No. 249,696 filed Mar. 31, 1981, now U.S. Pat. No. 4,374,853.

BACKGROUND OF THE INVENTION

This invention relates to novel lice-killing compositions for the control of lice on animals, primarily humans, and to methods of controlling lice on such animals.

Pediculosis capitis is one of the more common forms of pediculosis in humans due to investation with the head louse, *Pediculus Humanus Humanus.* Transmission of the lice is usually by personal contact or common use of brushes, combs, or headgear.

*Pediculosis Captitis* is a lice infestation characterized by itching and possibly eczematous dermatitis. In long standing, neglected cases, scratching may result in marked inflammation. Secondary infection by bacteria may occur with formation of pustules, crusts, and suppuratim. The hair may become matted and give rise to a disgusting odor.

Another form of pediculosis, known as *Pediculosis Corporis* or pediculous vestimenti, is an infestation with the body louse *Pediculus Humanus Corporis.* P. Corpus is transmitted by direct contact or use of infested wearing apparel that typically occurs as the result or crowding or unhygenic conditions. Symptoms include intense itching while, in particular, heavy infestations generalized red skin eruptions, mild fever, tiredness, irritability and possibly weakness and debility may occur.

A third type is pediculosis pubis and is due to body infestation with the crablouse, *Phthirus Pubis* which is generally confined to the hairs of the genital region, but the hair of the axilla, eyebrows, eyelashes, beard, and in hairy individuals, body surface may be involved. Lice may be acquired from direct contact with another infested individual, wearing contaminated clothing, from toilet seats, or from bed clothes. Symptoms include itching, especially in the genital or crural regions; small pale-blue spots resulting from the action of salivary secretion on hemoglobin are characteristic. See generally *The Merck Manual,* 12th Edition, Merck & Co., Inc., pp. 1455-1457 and 1633-1634 (1972).

There are several treatments now used for these conditions. An ectoparasiticide connotes only those drugs that are used against the animal parasites; in the human these are categorized as primarily mitocides, such as for the treatment of scabies, a mite infestation; or pediculocides, for the treatment of lice. Previously proposed chemical treatments include the use of chlorophenothane (DDT) and gamma benzene hexachloride (Kwell), as the major ectoparasiticides. Also benzyl benzoate, pyrethrins, malathion, a combination of tetrahydronaphthalene and cupric oleate (Cuprex), isoboruyl thiocyanoacetate, sulfur ointment U.S.P. and sulfurated lime have been used. The use of each of these materials has been questioned as to precautions and potential adverse responses and/or effectiveness; see Goodman and Gilman, *The Pharmacological Basis of Therapeutics,* 5th Edition, pp. 1012-1015 (1975).

Other forms of treatment are physical in nature and include removal of the hair-infested areas in question, followed by washing with strong soap and optionally one of the ectoparasiticides listed above. Clothing or instruments in contact with the affected body parts are also to be sterilized, such as by dry heat (140° F. for five minutes), hot water (150° F. for five minutes) or dry cleaning.

Lice infestation is a world-wide and growing concern, particularly in recent years in the United States among primary school students, and is often embarrassing as it was previously associated only with overcrowded conditions where inadequate facilities for personal hygiene or clean clothing exist. Pediculocides previously employed have now come under more careful examination and review and certain of the more commonly used materials, such as DDT and malathion, may be or have been discontinued. A need remains for a safe yet thoroughly effective pediculocide composition useful for animals, particularly humans.

DESCRIPTION OF THE INVENTION

My invention includes pediculicide compositions and methods of eradicating body lice using these compositions. The compositions comprise individual ingredients each of which is recognized as safe enough for topical, and in the case of one component internal, human use.

The pediculicide compositions of my invention include the following three ingredients: at least one pediculus-effective surface active wetting agent, benzyl salicylate, and an alcohol, preferably present in a weight ratio of 1:1:2, respectively. While I do not wish to be bound to any particular theory, it appears that the chemical action of the surface active wetting agent, for example the preferred surfactant dioctyl sodium sulfosuccinate (DSS), with benzyl salicylate produces a response more effective than the individual use of each ingredient. In particular benzyl salicylate is an important component of the compositions of my invention.

As the surface-active pediculus-effective surface active agent, one can use one or more of any suitable synthetic detergent active compounds which are readily available in commerce and described in the literature, for example in "Surface Active Agents and Detergents," Volumes 1 and 2 by Schwartz, Perry and Berch. Generally stated, the surface active component may include a synthetic anionic, nonionic, amphoteric or zwitterionic compound or mixtures of two or more of these compounds.

The preferred surface active agent is sodium or calcium dioctyl sulfosuccinate because the material is well tolerated and the calcium salt is accepted for internal use in the human body as a cathartic; see *The Merck Index,* 9th Edition, monograph 3287 and 3288 (1976). Thus, from the above grouping a selection will be made of a pharmaceutically appropriate and effective surface active agent which when used together with the benzyl salicylate aqueous solution provides a safe yet effective pediculicide composition.

As the alcohol component of the compositions one may select from $C_1$-$C_4$ alkanols, with isopropyl alcohol the preferred material. The alcohol acts as a solvent and vehicle for the other components of the composition. Benzyl salicylate is the third essential component.

The compositions of my invention may take several pharmaceutical forms, such as shampoos, creams, oils, aerosols or pump sprays and powders, in which the active ingredients are absorbed upon an inert carrier, as well as hair creams, sprays, rinses and lotions. The compositions may be applied to the lice-infested area, or preferably to the animals entire body, for effective lice control and eradication. The compositions described herein are concentrates in that they may be diluted with water or other diluent to a strength so that remains effective for killing body lice. One will thus select an appropriate concentration to be economical yet effective for the infestation to be controlled/treated.

Usual pharmaceutical formulating and aesthetic agents may be included in the novel compositions and are included within the scope of my invention. They include colorants, perfumes and agents included to achieve acceptable, well-tolerated pharmaceutically elegant formulation.

The preferred composition consists, in percent by weight, of the following:

| Ingredient | Range | Preferred |
| --- | --- | --- |
| dioctyl sodium sulfosuccinate | 10-25 | 25 |
| benzyl salicylate | 10-50 | 25 |
| isopropyl alcohol | balance | 50 |

The compositions can comprise, consist essentially or consist of the materials set forth and the process or method can comprise, consist essentially or consists of the steps set forth with such materials.

It will be understood that while my invention has been described with respect to eradicating or controlling lice infestations in animals, particularly lice on humans, there are numerous other applications to which the compositions of my invention may be put. Also in explaining my invention reference is herein made to various specific procedures and methods for accomplishing the desired result of eradicating or controlling lice of the type described above on warm blooded animals. It will be understood that other procedures and methods are contemplated herein for the desired insect control in addition to those specifically described, utilizing the compositions of my invention.

My invention will now be further illustrated with reference to the following example. Unless otherwise indicated all parts and percentages are by weight and all temperatures are reported in degrees centigrade.

DETAILED DESCRIPTION OF THE INVENTION

The compositions of the invention were tested to determine their effectiveness a pediculicidal materials in liquid form against the adult human louse, *Pediculus Humanus*. In summary, four replicates of 25 lice each, plus at least one control for each batch of lice, was used for each concentration, dipping time variable or any other variable tested.

Ratings and observations are reported as follows:

Morbid—unable to move towards heat one hour after treatment: sickly, but not necessarily dying; may recover by 24 hours.

Moribund—unable to move towards heat, and therefore, 24 hours after treatment; dying. Next, the patch containing the eggs was placed in a plastic container (10 cm×7 cm) with a screened lid, and the date noted on container. The container was incubated at 31.7° C. (89° F.) and 60% relative humidify. The eggs hatched in approximately 8 days and a blood meal was provided on the 9th day.

Blood meals were served daily. The lice were allowed to feed on the shaved abdomen of a restrained rabbit. The rabbit was placed on its back on the restraining rack for approximately 30 minutes. The lice were collected after feeding by moving the corduroy patches back and forth gently over the shaved area of the rabbit. Most of the lice attached to the path; any remaining lice were picked up with a forceps or camels hair brush.

Lice used for testing were usually 17±1 day old, as determined from the date of the first blood meal. Adult lice, for egg laying purposes, were kept approximately three weeks from time of hatching then discarded.

Twenty-five adult lice, mixed sexes, were placed in the bottom of the 9 dram test container screened at the bottoms with 20 mesh screen. A screened plunger made from a plastic rod covered at one end with a 20 mesh screen was inserted to keep the lice from floating to the surface. The insecticide to be tested was placed in 100 ml beaker and introduce the beaker into a waterbath maintained at 32° C. The test container was dipped into the insecticide in the 100 ml beaker and the lice were under the pesticide for 2 minutes.

The test concentrate consisted of the following, in percent by weight:
dioctyl sodium sulfosuccinate: 25%,
benzyl salicylate: 25%,
isopropyl alcohol: 50%.

Next the test container was removed at the end of desired dipping period and the bottom of the container blotted to remove remaining liquid. The container was dipped into the 1,000 ml beaker containing distilled water at 32° C. and agitated. At the end of one minute, the container was removed and the lice were gently washed in a stream of distilled water at 32° C. from a wash bottle. Excess water was blotted with paper toweling.

The lice were transferred to a clean 4×4 cm patch of dark corduroy cloth and a camels hair brush was used to remove any lice that remain in the container. The corduroy patch was placed in a petri dish 8.9 cm in diameter and 1.3 cm deep. The petri dish with lice was then placed in an incubator maintained at 31.7° C. and 60% RH.

The first observation was made 1 hour following treatment and the petri dish returned to incubator.

Observations were made as follows: the patch with lice was placed on top of a clean patch on the plate of a slide warmer (37° C.). Lice not dead or morbid moved to the lower patch. For the non-treated control, all of the above procedures were repeated except distilled water was substituted for the candidate pediculicide. Observations were repeated in 24 hours to separate living lice from dead and moribund ones (see the above rating scale).

The data collected were converted to percentages. Dead and moribund lice were added together to give mortality at 24 hours. Mortalities among treated lice were corrected by Abbott's formula, Abbott, W. S. (1925), "A Method of Computing the Effectiveness of an Insecticide," J. Econ. Ent. 18: 265-267. This correction allows by any natural mortality which occurred during the test.

$$\text{Correct Mortality} = \frac{(\% \text{ Alive in Control}) - (\% \text{ Alive in Test})}{(\% \text{ Alive in Control})} \times 100$$

The results of the testing are as follows:

| Time | Adult Louse Mortality | | |
|---|---|---|---|
| | Alive | Moribund | Dead |
| +1 hour | 0 | 0 | 25 |
| +24 hours | 0 | 0 | 25 |

The test insect used was the human louse, *Pediculus Humanus Humanus*. This strain is available from Insect Control & Research, Inc., Baltimore, Md. 21228 and was established from the USDA Gainesville strain. It is a susceptible strain and, through selection, has adapted to a rabbit host.

What is claimed is:

1. A method of killing lice on warm-blooded animals comprising the steps of:
   (a) applying to said animal a pediculicidely-effective amount of a composition consisting essentially of an alcohol solution of from 10 to about 25 weight percent benzyl salicylate and from 10 up to about 50 weight percent of at least one compatible, pediculicidely-effective surface active wetting agent incorporated therein, the balance of the solution being said alcohol;
   (b) allowing the thus applied composition to remain in contact with the infested area for a period of time sufficient to kill the lice contained therein, and thereafter
   (c) removing the composition and killed lice.

2. The method of claim 1 wherein said composition comprises a solution of benzyl salicylate and isopropyl alcohol present in a ratio of about 1:2.

3. The method of claim 1 wherein said pediculicidely-effective surface active agent is dioctyl sodium sulfosuccinate, dioctyl calcium sulfosuccinate or a mixture of the two.

4. The method of claim 1 wherein said composition consists essentially of benzyl salicylate, isopropyl alcohol and a salt of dioctyl sulfosuccinate.

5. A pediculicide composition for killing lice on a warm blooded animal consisting essentially, in percent by weight, of:
   dioctyl sodium or calcium sulfosuccinate: about 10 to about 25,
   benzyl salicylate: about 10 to about 50,
   isopropyl alcohol: balance.

6. A pediculicide composition for killing lice on a warm blooded animal consisting essentially of dioctyl sodium and/or calcium sulfosuccinate, benzyl salicylate and isopropyl alcohol present in a weight ratio of about 1:1:2, respectively.

* * * * *